(12) United States Patent
Matsushima et al.

(10) Patent No.: US 9,138,176 B2
(45) Date of Patent: Sep. 22, 2015

(54) BIOLOGICAL INFORMATION MEASURING DEVICE AND CONTROL METHOD THEREOF

(75) Inventors: Hideki Matsushima, Osaka (JP); Masao Nonaka, Osaka (JP); Natsume Matsuzaki, Osaka (JP); Yuichi Futa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1132 days.

(21) Appl. No.: 13/133,037

(22) PCT Filed: Dec. 11, 2009

(86) PCT No.: PCT/JP2009/006777
§ 371 (c)(1),
(2), (4) Date: Jun. 6, 2011

(87) PCT Pub. No.: WO2010/079554
PCT Pub. Date: Jul. 15, 2010

(65) Prior Publication Data
US 2011/0238324 A1  Sep. 29, 2011

(30) Foreign Application Priority Data

Jan. 7, 2009  (JP) ................................. 2009-001817

(51) Int. Cl.
*G01N 21/01* (2006.01)
*G01N 21/17* (2006.01)
(Continued)

(52) U.S. Cl.
CPC ................. *A61B 5/117* (2013.01); *A61B 5/489* (2013.01); *G06T 7/0016* (2013.01); *G06T 2207/10048* (2013.01); *G06T 2207/10152* (2013.01); *G06T 2207/30101* (2013.01)

(58) Field of Classification Search
CPC ....................................................... A61B 5/00

USPC ......... 702/19, 21, 23, 56, 189, 190; 340/5.83; 382/115, 124, 128
See application file for complete search history.

(56) References Cited

U.S. PATENT DOCUMENTS 7,672,488 B2 * 3/2010 Miura et al. .................. 382/115
8,055,031 B2 * 11/2011 Asano et al. ................. 382/124
(Continued)

FOREIGN PATENT DOCUMENTS

JP  2003-299624  10/2003
JP  2005-253478  9/2005
(Continued)

OTHER PUBLICATIONS

International Search Report issued Jan. 26, 2010 in corresponding International Application No. PCT/JP2009/006777.
(Continued)

*Primary Examiner* — Eliseo Ramos Feliciano
*Assistant Examiner* — Felix Suarez
(74) *Attorney, Agent, or Firm* — Wenderoth, Lind & Ponack, L.L.P.

(57) ABSTRACT

A biological information measuring device includes a finger insertion part; a first light source which emits, to the finger insertion part, first light; a second light source which emits, to the finger insertion part, second light; and a first light-receiving unit which receives first reception light which is the first light transmitted through the finger or reflected from the finger. A second light-receiving unit receives second reception light which is the second light transmitted through the finger or reflected from the finger; a calculating unit measures a vein pattern of the user based on the first reception light, and measures biological data of the user based on the second reception light; and a transmitting and receiving unit transmits, to an external server, a measurement result of the vein pattern and a measurement result of the biological data.

16 Claims, 8 Drawing Sheets

(51) Int. Cl.
  *G01N 21/25* (2006.01)
  *H03F 3/38* (2006.01)
  *A61B 5/117* (2006.01)
  *A61B 5/00* (2006.01)
  *G06T 7/00* (2006.01)

(56) References Cited

U.S. PATENT DOCUMENTS

2002/0013717 A1   1/2002   Ando et al.
2005/0180620 A1*  8/2005   Takiguchi ............... 382/128
2007/0177771 A1   8/2007   Tanaka et al.

FOREIGN PATENT DOCUMENTS

| | | |
|---|---|---|
| JP | 2007-35050 | 2/2007 |
| JP | 2007-105331 | 4/2007 |
| JP | 2007-202869 | 8/2007 |
| JP | 2008-250821 | 10/2008 |
| JP | 2008-289808 | 12/2008 |

OTHER PUBLICATIONS

Reply submitted in International Application No. PCT/JP2009/006777 filed on Dec. 11, 2009 (with partial English translation).

* cited by examiner

FIG. 3
Blood sugar level management memory 203
| User ID | Vein information | Measurement log | | |
|---------|------------------|-----------|-----|-----------|
| ID1 | Vein img1 | Region 11 | ... | Region 1m |
| : | | | | |
| IDn | Vein imgn | Region n1 | ... | Region nm |
FIG. 4
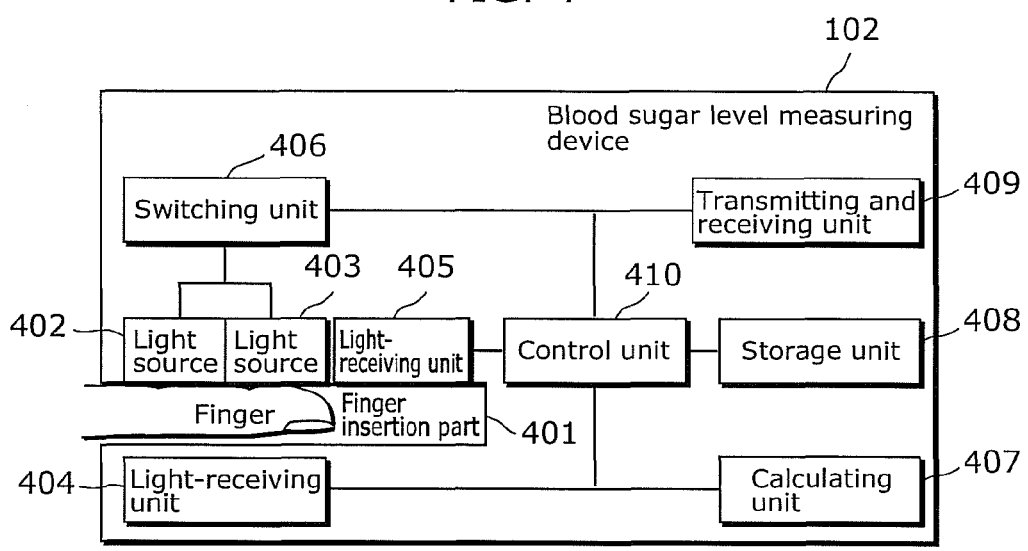
FIG. 5
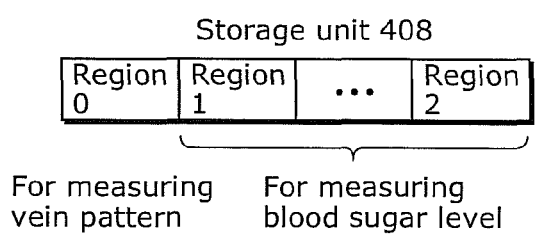

(a) Data to be transmitted (at the time of initial registration)

| User ID | Measurement result of vein pattern |
|---|---|

(b) Data to be transmitted (at the time of measuring blood sugar level)

| Measurement result of blood sugar level | Measurement result of vein pattern |
|---|---|

FIG. 13
(a) First measurement
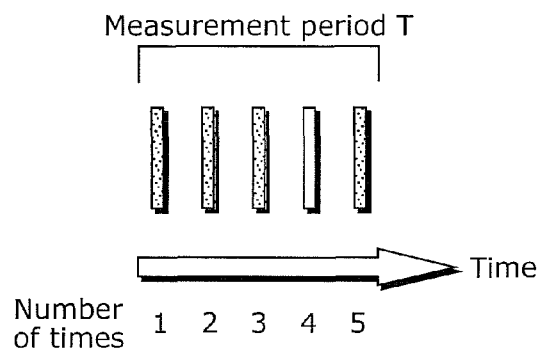
(b) Second measurement
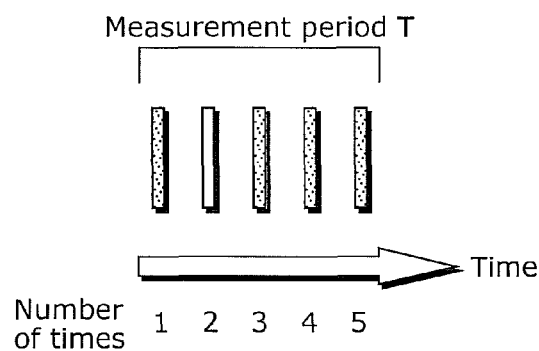
(c) Third measurement
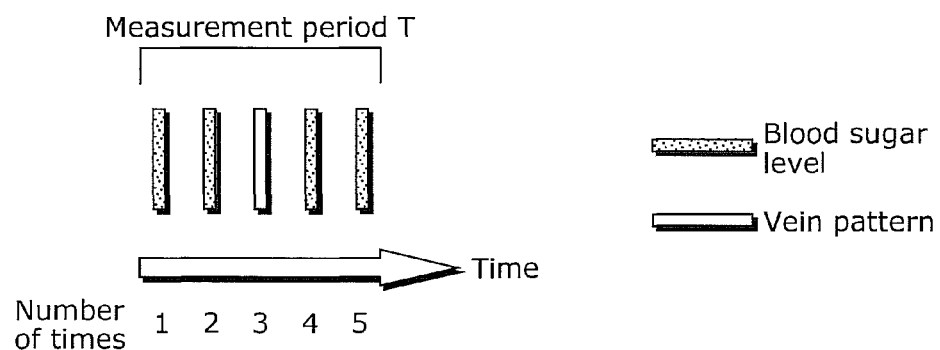

BIOLOGICAL INFORMATION MEASURING DEVICE AND CONTROL METHOD THEREOF

BACKGROUND OF INVENTION

Technical Field

The present invention relates to biological information measuring devices which measure biological data and control methods thereof, and in particular to a biological information measuring device which measures a blood sugar level and a control method thereof.

BACKGROUND ART

Taking, as an example, a blood sugar level as biological data of a patient, in recent years, measuring devices which non-invasively analyze a state of hemoglobin A1c in blood have been considered. Conventionally, the hemoglobin A1c has been clinically used as an index for diagnosing diabetes or identifying a state of blood sugar control.

The measuring devices analyze the hemoglobin A1c in blood by emitting light to a finger or the like, without requiring collection of blood in the analysis. In the analysis of the hemoglobin A1c in blood, the measuring devices analyze, using light having a predetermined wavelength, a ratio at which the hemoglobin A1c in blood and glucose are combined. With this, a blood sugar level test can be non-invasively performed without requiring collection of blood in the test, and thus patients can take the test without feeling pain or stress (Patent Literature 1, for instance).

CITATION LIST

Patent Literature

[PTL 1]
Japanese Unexamined Patent Application Publication No. 2005-253478

SUMMARY OF INVENTION

However, the above conventional technique causes the following problem.

In the conventional technique, to transfer a test result between a doctor and a patient, either a patient has to bring the test result to a hospital or a doctor, a nurse, or the like has to visit the patient's home to directly receive the test result. Consequently, it is inconvenient for both the doctor and the patient.

The above problem can be solved by providing a communication function to a measuring device and transmitting the test result of the patient to a server placed in the hospital.

However, when patients transmit respective test results to the server, not including, in data to be transmitted, information for identifying a corresponding one of the patients of the respective test results does not make it possible to identify the corresponding one of the patients of the respective test results on the server side. More specifically, to identify a patient, it is conceivable to pre-set, to a measuring device, a unique ID for identifying the measuring device, and transmit, to the server, a test result together with the ID of the measuring device.

In this case, however, because the unique ID is pre-set to the measuring device, when the patient loses the measuring device, there is a chance that a third person who finds the measuring device secretly looks at the test result of the patient based on the ID. As a result, there is a problem that privacy of patients cannot be protected.

The present invention has been devised in view of the above problem, and has an object to provide a biological information measuring device which is capable of protecting privacy of users, and a control method thereof.

In order to solve the above problem, a biological information measuring device according to an aspect of the present invention includes: a finger insertion part into which a finger of a user is inserted; a first light source which emits, to the finger insertion part, first light having a first wavelength; a second light source which emits, to the finger insertion part, second light having a second wavelength different from the first wavelength; a first light-receiving unit configured to receive first reception light which is the first light transmitted through the finger or reflected from the finger; a second light-receiving unit configured to receive second reception light which is the second light transmitted through the finger or reflected from the finger; a calculating unit configured to measure a vein pattern of the user based on the first reception light, and measure biological data of the user based on the second reception light; and a transmitting and receiving unit configured to transmit, to an external server, a measurement result of the vein pattern and a measurement result of the biological data.

With this configuration, the measurement result of the vein pattern is transmitted instead of a user ID. For this reason, when the server performs authentication using the measurement result of the vein pattern, the server makes it possible to manage the biological data of the user using, instead of the user ID, the measurement result of the vein pattern obtained each time the biological data is measured. This does not leave personal information of the user in the biological information measuring device. Thus, even when the user loses the biological information measuring device, a third person cannot access the biological information measuring device to secretly look at the personal information of the user. As a result, the biological information measuring device makes it possible to protect privacy of the user.

It is to be noted that the present invention may be implemented not only as the biological information measuring device including such characteristic processing units, but also as a control method of the biological information measuring device, which includes, as steps, the characteristic processing units of the biological information measuring device, and as a program causing a computer to execute the characteristic steps included in the control method of the biological information measuring device. It goes without saying that such a program can be distributed via a computer-readable recording medium such as a CD-ROM (Compact Disc-Read Only Memory) or a communication network such as the Internet.

The present invention makes it possible to provide the biological information measuring device which is capable of protecting the privacy of the users, and the control method thereof.

BRIEF DESCRIPTION OF DRAWINGS

FIG. 3 is a diagram showing a data structure in a blood sugar level management memory of the authentication server according to the embodiment of the present invention.

FIG. 4 is a block diagram showing an internal configuration of a blood sugar level measuring device according to the embodiment of the present invention.

FIG. 5 is a diagram showing a data structure in a storage unit of the blood sugar level measuring device according to the embodiment of the present invention.

FIG. 13 is a diagram showing a change of a vein pattern measurement timing.

DETAILED DESCRIPTION OF INVENTION

The following describes a biological information measuring system according to an embodiment of the present invention, with reference to the drawings. It is to be noted that this embodiment gives the description, using a blood sugar level as an example of biological data.

Figure 1:
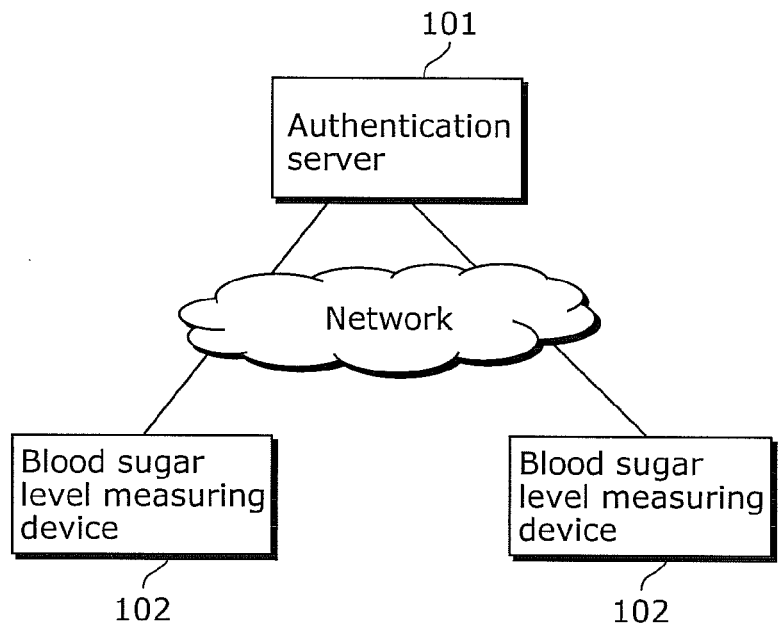
FIG. 1 is a diagram showing a configuration of a biological information measuring system according to an embodiment of the present invention.

FIG. 1 is a diagram showing a configuration of a biological information measuring system according to this embodiment of the present invention. In FIG. 1, the biological information measuring system according to this embodiment includes an authentication server 101 and blood sugar level measuring devices 102. The authentication server 101 and the blood sugar level measuring devices 102 are mutually connected via a network. Here, the network includes a wired network such as Ethernet™, a wireless network such as a wireless LAN (Local Area Network), or a network obtained by combining those.

The authentication server 101 collects, from each of the blood sugar level measuring devices 102, a measurement result of a vein pattern of a user, and authenticates the user. In addition, the authentication server 101 collects, from the blood sugar level measuring device 102, a measurement result of a blood sugar level, and registers the collected measurement result into a database.

The blood sugar level measuring device 102 measures a blood sugar level of a user as well as information for authenticating the user (hereinafter, referred to as "measurement for personal authentication"). In the measurement for personal authentication, a vein pattern of the user is measured as the information for authenticating the user. Moreover, the blood sugar level measuring device 102 communicates with the authentication server 101, and transmits, to the authentication server 101, a measurement result of the vein pattern and a measurement result of the blood sugar level.

Figure 2:
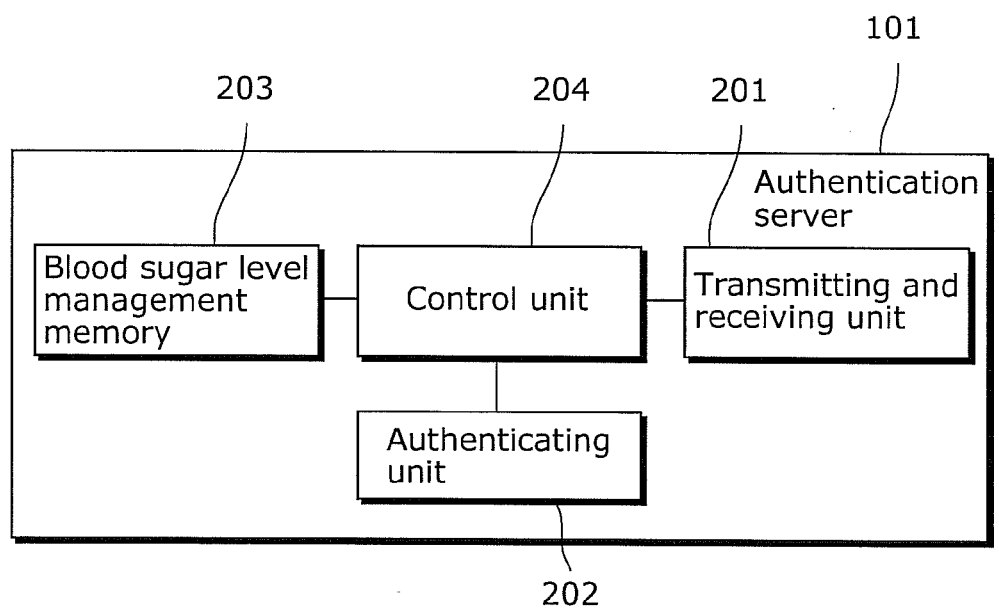
FIG. 2 is a block diagram showing an internal configuration of an authentication server according to the embodiment of the present invention.

FIG. 2 is a block diagram showing an internal configuration of the authentication server 101 according to this embodiment of the present invention. In FIG. 2, the authentication server 101 according to this embodiment includes a transmitting and receiving unit 201, an authenticating unit 202, a blood sugar level management memory 203, and a control unit 204.

The transmitting and receiving unit 201 communicates with the blood sugar level measuring device 102 via the network. At the time of initial user ID registration, the transmitting and receiving unit 201 receives, from the blood sugar level measuring device 102, a user ID and a measurement result of a vein pattern to be set for authenticating the user. At the time of blood sugar level measurement, the transmitting and receiving unit 201 receives, from the blood sugar level measuring device 102, a measurement result of a vein pattern and a measurement result of a blood sugar level. In addition, at the time of the blood sugar level measurement, the transmitting and receiving unit 201 transmits, to the blood sugar level measuring device 102, an authentication result of the user, that is, information indicating whether or not the user has been successfully authenticated.

The authenticating unit 202 authenticates the user, using the measurement result of the vein pattern of the user.

The blood sugar level management memory 203 stores, for each user, a measurement result of a blood sugar level of the user and a measurement result of a vein pattern of the user to be set for authenticating the user. A detailed data structure in the blood sugar level management memory 203 is later described with reference to FIG. 3.

The control unit 204 controls operations of each of the transmitting and receiving unit 201, the authenticating unit 202, and the blood sugar level management memory 203. In addition, the control unit 204 transfers, to each of the above units, information necessary for each unit such as a measurement result of a blood sugar level, a measurement result of a vein pattern, and an authentication result.

FIG. 3 is a diagram showing in detail a data structure in the blood sugar level management memory 203 shown in FIG. 2. In FIG. 3, the blood sugar level management memory 203 stores, for each user, information about each of item "user ID", item "vein information", and item "measurement log".

An ID for identifying a user using the blood sugar level measuring device 102 is stored in the item "user ID". Information about a measurement result of a vein pattern of a user registered at the time of initial user ID registration is stored in the item "vein information". This vein information is used as a determination criterion for authentication. A measurement result of a blood sugar level is stored in the item "measurement log".

In the case shown in FIG. 3, the blood sugar level management memory 203 stores vein information and a measurement log of each of n users having respective user IDs "ID1" to "IDn". For instance, for the user having "ID1" in the item "user ID", "vein img1", which is image data of a vein pattern of the user, is registered in the item "vein information". Moreover, for the user having "ID1", "region 11" to "region 1$m$" in which m measurement results of respective blood sugar levels are stored are held in the item "measurement log". Likewise, for the user having "IDn" in the item "user ID", "vein imgn", which is image data of a vein pattern of the user, is registered in the item "vein information". Moreover, for the user having "IDn", "region n1" to "region nm" in which m measurement results of respective blood sugar levels are stored are held in the item "measurement log".

FIG. 4 is a block diagram showing an internal configuration of the blood sugar level measuring device 102 according to this embodiment of the present invention. In FIG. 4, the blood sugar level measuring device 102 according to this embodiment includes a finger insertion part 401, light sources 402 and 403, light-receiving units 404 and 405, a switching unit 406, a calculating unit 407, a storage unit 408, a transmitting and receiving unit 409, and a control unit 410. It is to be noted that the switching unit 406, the storage unit 408, and the control unit 410 are not essential elements of the present invention.

The finger insertion part 401 is a component into which a finger of a user is inserted, and is an area having a hole into which the finger of the user is inserted. The finger insertion part 401 is provided inward from a side of the blood sugar level measuring device 102. The user of the blood sugar level measuring device 102 measures a blood sugar level of the user by inserting a finger of the user into the finger insertion part 401. The light sources 402 and 403 are provided on the same surface of an external wall of the finger insertion part 401.

The light source 402 emits, to the finger insertion part 401, infrared light (hereinafter, referred to as "first infrared light") having, for example, the wavelength of 760 nm. The light-receiving unit 404 is provided to place the finger insertion part 401 between the light-receiving unit 404 and the light source 402, and receives transmitted light which is the first infrared light transmitted through the finger. A vein pattern of the user is measured based on the transmitted light of the first infrared light received by the light-receiving unit 404. In addition, the light-receiving unit 404 detects that the user has inserted the finger into the finger insertion part 401, by receiving the transmitted light of the first infrared light. It is to be noted that the wavelength of the first infrared light is not limited to 760 nm as long as the wavelength allows a vein pattern to be measured.

In contrast, when biological data to be measured is a blood sugar level, the light source 403 emits, to the finger insertion part 401, infrared light (hereinafter, referred to as "second infrared light") having, for example, the wavelength of 1300 nm. The light-receiving unit 405 is placed to face the finger insertion part 401 and to be on the same side as the light source 402, and receives reflected light which is the second infrared light reflected from the user's finger inserted into the finger insertion part 401. A blood sugar level of the user is measured based on the reflected light of the second infrared light received by the light-receiving unit 405. It is to be noted that the wavelength of the second infrared light is not limited to 1300 nm as long as the wavelength allows biological data to be measured.

The switching unit 406 switches between the light sources 402 and 403 depending on whether a vein pattern or a blood sugar level is to be measured. More specifically, the switching unit 406 switches between the light sources 402 and 403 so that the light source 402 emits light when the vein pattern is to be measured or insertion of a user's finger is to be detected and that the light source 403 emits light when the blood sugar level is to be measured.

The calculating unit 407 measures the vein pattern of the user based on the transmitted light of the first infrared light received by the light-receiving unit 404. In addition, the calculating unit 407 measures the blood sugar level of the user based on the reflected light of the second infrared light received by the light-receiving unit 405.

The calculating unit 407 measures biological data a predetermined number of times in a predetermined measurement period, determines a value obtained from measurement results of respective biological data measured the predetermined number of times as one measurement result of biological data, and measures the vein pattern in the predetermined measurement period. It is to be noted that the calculating unit 407 measures the vein pattern of the user with a timing determined by the control unit 410.

The storage unit 408 stores the measurement result of the vein pattern and the measurement result of the blood sugar level. A detailed data structure in the storage unit 408 is later described with reference to FIG. 5. It is to be noted that the measurement result of the vein pattern is image data of the vein pattern.

The transmitting and receiving unit 409 communicates with the authentication server 101 via the network. At the time of the initial user ID registration, the transmitting and receiving unit 409 transmits, to the authentication server 101, the user ID of the user and the measurement result of the vein pattern to be registered for authenticating the user. On the other hand, at the time of the blood sugar level measurement, the transmitting and receiving unit 409 transmits, to the authentication server 101, the measurement result of the vein pattern and the measurement result of the blood sugar level. In addition, at the time of the blood sugar level measurement, the transmitting and receiving unit 409 receives, from the authentication server 101, an authentication result of the user obtained by using the measurement result of the vein pattern, that is, information indicating whether or not the user has been successfully authenticated.

The control unit 410 controls operations of each of the light-receiving units 404 and 405, the switching unit 406, the calculating unit 407, the storage unit 408, and the transmitting and receiving unit 409. In addition, the control unit 410 transfers, between the above units, information necessary for each of the units such as a measurement result of a blood sugar level and a measurement result of a vein pattern. Further, the control unit 410 determines a timing at which a vein pattern is to be measured (vein pattern measurement timing) for each predetermined period. For instance, when a blood sugar level and a vein pattern are measured four times and once, respectively, in a predetermine measurement period, the control unit 410 determines a timing at which a vein pattern of a user is to be measured so that the timing changes for each predetermined measurement period. In more detail, the control unit 410 determines the timing at which the vein pattern of the user is to be measured so that the timing randomly changes for each predetermined measurement period.

FIG. 5 is a diagram showing in detail a data structure in the storage unit 408 shown in FIG. 4. In FIG. 5, the storage unit 408 includes a region in which a measurement result of a vein pattern is stored and regions in each of which a measurement result of a blood sugar level is stored. In the case shown in FIG. 5, "region 0" is designated as a region in which a measurement result of a vein pattern to be used for authenticating a user is stored. In contrast, "region 1" to "region n" are designated as regions in which first to n-th measurement results of respective blood sugar levels are stored.

Figures 6, 7:
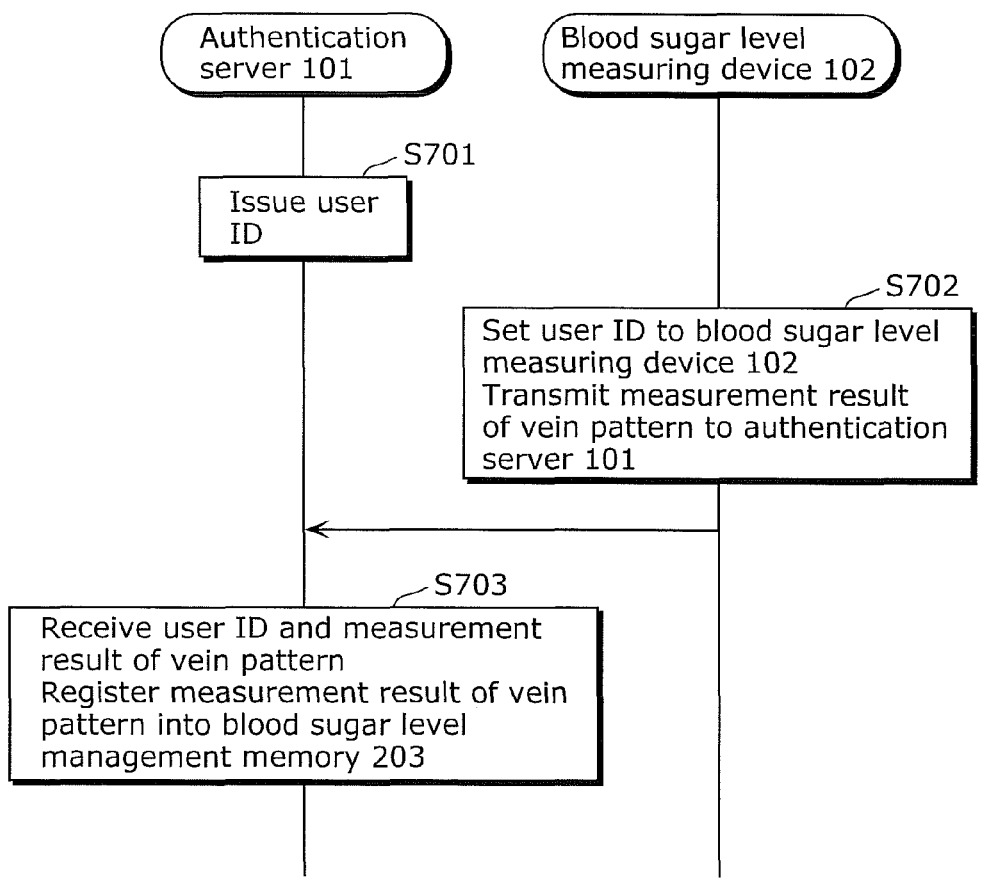
FIG. 6 is a diagram showing data structures of data transmitted from the blood sugar level measuring device to the authentication server in the biological information measuring system according to the embodiment of the present invention.
FIG. 7 is a sequence diagram showing operations of the blood sugar level measuring device and the authentication server at the time of initial user ID registration, in the biological information measuring system according to the embodiment of the present invention.

FIG. 6 shows data structures of data transmitted from the transmitting and receiving unit 409 of the blood sugar level measuring device 102 to the authentication server 101. (a) in FIG. 6 shows a data structure of data to be transmitted when a user initially registers a user ID of the user into the authentication server 101. (b) in FIG. 6 shows a data structure of data to be transmitted when the user measures a blood sugar level of the user.

More specifically, in the case of (a) in FIG. 6, that is, in the case of the initial registration, the data to be transmitted includes a user ID and a measurement result of a vein pattern to be set for authenticating a user, which are for identifying the user. In addition, here, the user may measure a blood sugar level of the user, and transmit a measurement result of the blood sugar level together with the measurement result of the vein pattern of the user.

In contrast, in the case of (b) in FIG. 6, that is, in the case of the blood sugar level measurement, the data to be transmitted includes a measurement result of a vein pattern and a measurement result of a blood sugar level. Here, the measurement result of the blood sugar level included in the data to be transmitted is calculated based on first to n-th measurement results of respective blood sugar levels stored in "region 1" to "region n" of the storage unit 408. For example, when a blood sugar level is measured four times to obtain one measurement result, conceivable is method for using an average value of the four measurement results as the measurement result of the blood sugar level to be transmitted to the authentication server 101. Moreover, conceivable is a method for excluding the maximum and minimum values from the four measurement results and using an average value of the remaining two measurement results.

The following describes operations of the biological information measuring system thus configured, with reference to the drawings.

FIG. 7 is a sequence diagram showing operations of the authentication server 101 and the blood sugar level measuring device 102 at the time of the initial user ID registration, in the biological information measuring system according to this embodiment of the present invention. In this processing, a user ID and a measurement result of a vein pattern of a user are registered into the authentication server 101.

A doctor, a nurse, or the like at a hospital issues a user ID beforehand, and initially registers the issued user ID into the authentication server 101 (S701).

A user receives the user ID at the reception of the hospital. Then, the user sets the received user ID to the blood sugar level measuring device 102 of the user. The user uses the blood sugar level measuring device 102, to which the user ID is set, to measure a vein pattern of the user. After the vein pattern is measured, the blood sugar level measuring device 102 transmits, to the authentication server 101, the user ID and a measurement result of the vein pattern (S702). Here, the blood sugar level measuring device 102 sets the user ID and the measurement result of the vein pattern in data to be transmitted as shown in (a) in FIG. 6, and transmits the data to the authentication server 101.

When the transmitting and receiving unit 201 of the authentication server 101 receives the user ID and the measurement result of the vein pattern that are transmitted by the blood sugar level measuring device 102, the control unit 204 registers the received user ID and the received measurement result of the vein pattern in the item "user ID" and the item "vein information", respectively, of the blood sugar level management memory 203 shown in FIG. 3.

This allows the authentication server 101 to associate the user ID with the measurement result of the vein pattern. For this reason, at the time of blood sugar level measurement, a measurement result of a vein pattern measured each time a blood sugar level is measured is used by the authentication server 101 to authenticate a user and can be shared as an ID for identifying a blood sugar level of each of users.

Figure 8:
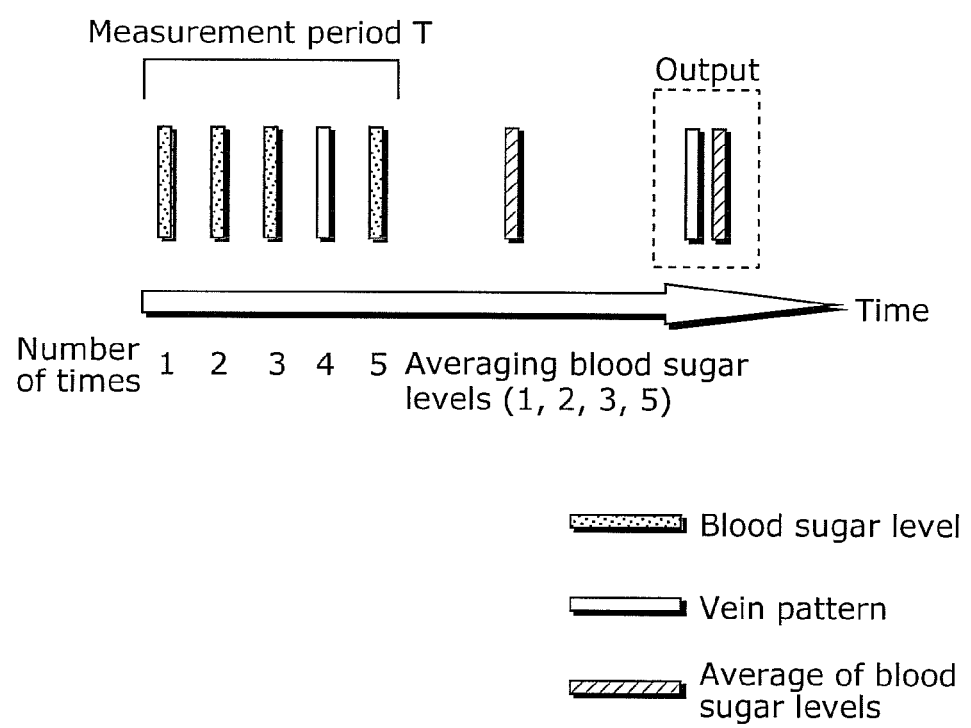
FIG. 8 is a diagram for illustrating a blood sugar level measurement principle used by the blood sugar level measuring device according to the embodiment of the present invention.

FIG. 8 is a diagram for illustrating a blood sugar level measurement principle used by the blood sugar level measuring device 102.

In order to obtain one measurement result of a blood sugar level, the blood sugar level measuring device 102 measures a blood sugar level a predetermined number of times in a predetermined measurement period "T". Then, the blood sugar level measuring device 102 determines the one measurement result of the blood sugar level by calculating an average of the measurement results of the respective blood sugar levels obtained by performing the measurement the predetermined number of times. In the case shown in FIG. 8, in order to obtain the one measurement result of the blood sugar level, the blood sugar level measuring device 102 measures the blood sugar level four times in the predetermined measurement period "T". Thus, an average of the four measurement results is determined as the one measurement result of the blood sugar level.

Moreover, the blood sugar level measuring device 102 measures a vein pattern in the predetermined measurement period "T", and changes a vein pattern measurement timing for each predetermined measurement period "T". For instance, FIG. 8 shows, as an example, a case where the vein pattern is measured between the third and fourth blood sugar level measurements in the predetermined measurement period "T". In other words, in FIG. 8, the blood sugar levels are measured the first, second, third, and fifth times, and the vein pattern is measured the fourth time. It is to be noted that, in an initial state where a blood sugar level has not been measured the first time in the predetermined measurement period "T", at which timing the vein pattern is measured is undecided for the blood sugar level measuring device 102.

In order to obtain the one measurement result of the blood sugar level, the blood sugar level measuring device 102 measures the blood sugar level the predetermined number of times in the predetermined measurement period "T", and determines the one measurement result of the blood sugar level by calculating the average of the measurement results obtained by performing the measurement the predetermined number of times. Moreover, the blood sugar level measuring device 102 measures the vein pattern in the predetermined measurement period "T", and changes the vein pattern measurement timing for each predetermined measurement period "T". With this, the blood sugar level measuring device 102 does not separate the blood sugar level measurements and the vein pattern measurement in terms of time but makes it possible to perform the measurements simultaneously. In addition, changing the vein pattern measurement timing for each predetermined measurement period "T" prevents the user from distinguishing between a vein pattern measurement timing and a blood sugar level measurement timing. Therefore, the third person cannot replace the finger of the user by the finger of the third person and measure the blood sugar level during a blood sugar level measurement. As a result, the blood sugar level measuring device 102 makes it possible to surely prevent the use of the measurement result of the blood sugar level of the third person as that of the user.

It is to be noted that the blood sugar level measuring device 102 may measure a blood sugar level at the first measurement among measurements performed in the predetermined measurement period "T". In this case, the first measurement is intended for measuring the blood sugar level, not a vein pattern. Thus, after measuring a vein pattern of the user the first time, it is not possible to replace the finger of the user by the finger of the third person and measure a blood sugar level of the third person the second time onward. As a result, it is possible to surely prevent the use of the measurement result of the blood sugar level of the third person as that of the user.

The following describes blood sugar level measurement processing performed by the blood sugar level measuring device 102.

Figure 9:
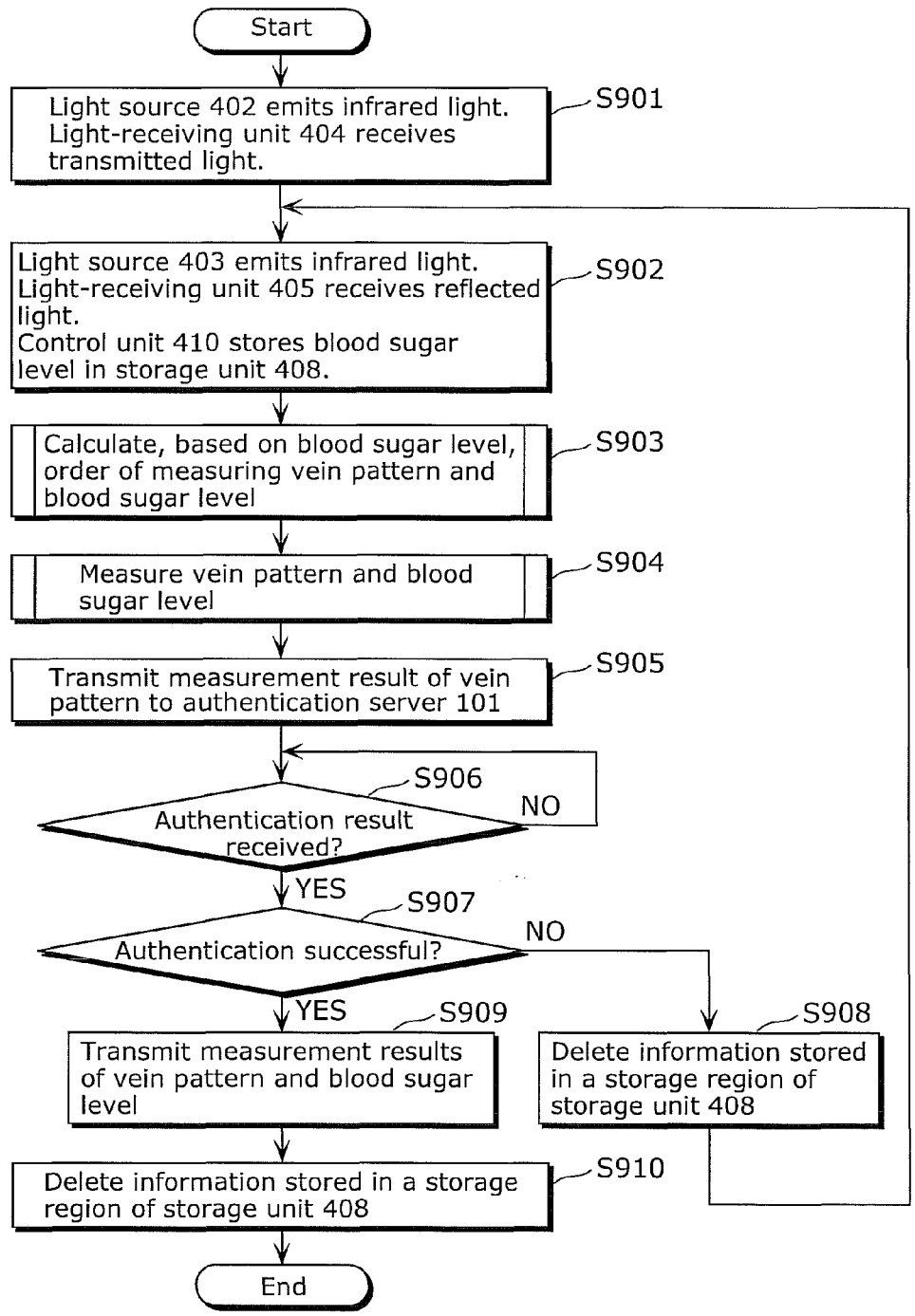
FIG. 9 is a flowchart showing operations of the blood sugar level measuring device according to the embodiment of the present invention.

FIG. 9 is a flowchart showing operations of the blood sugar level measuring device at the time of blood sugar level measurement.

In the operations, in order to obtain one measurement result of a blood sugar level, the blood sugar level measuring device 102 measures blood sugar levels and a vein pattern in a predetermined measurement period. The blood sugar level measuring device 102 then transmits, to the authentication server 101, the measurement results of the respective blood sugar levels and the measurement result of the vein pattern. It is to be noted that the control unit 410 controls each of the operations of the blood sugar level measuring device 102.

First, the user inserts the user's finger into the finger insertion part 401. After the finger insertion, the light source 402 emits the first infrared light to the finger insertion part 401 according to an instruction from the control unit 410. Then, the light-receiving unit 404 receives transmitted light which is the first infrared light emitted by the light source 402 and transmitted through the user's finger. Based on the transmitted light, the control unit 410 confirms that the user's finger has been inserted into the finger insertion part 401.

Next, the light source 403 emits the second infrared light to the finger insertion part 401 according to an instruction from the control unit 410. Then, the light-receiving unit 405 receives reflected light which is the second infrared light that has been emitted by the light source 403 and reflected from the user's finger. Here, the control unit 410 calculates a blood sugar level of the user based on the reflected light, and stores the blood sugar level in the storage unit 408 (S902). To put it differently, in S902, the first measurement of the blood sugar level among the four measurements of the respective blood sugar levels is performed. It is to be noted that a method for calculating a blood sugar level is not specifically limited to the above method, and may be a method for measuring a blood sugar level by analyzing, based on reflected light, a ratio at which the hemoglobin A1c in blood and glucose are combined (e.g., Patent Literature 1).

Next, the control unit 410 determines, based on information obtained from the reflected light received by the light-receiving unit 405 in S902, that is, the first measurement result of the blood sugar level, with which timing the vein pattern is to be measured, among the timings at which the blood sugar levels are to be measured, and determines order of measuring the blood sugar levels and the vein pattern. This process is later described with reference to FIG. 10.

Next, the control unit 410 measures, based on the order determined in S903, the blood sugar level three times and the vein pattern once while controlling the switching unit 406, and stores each of the measurement results in the storage unit 408 (S904). The switching unit 406 sets the light source 402 when the vein pattern is to be measured, and sets the light source 403 when the reflected light is to be received. This process is later described with reference to FIG. 11.

Next, the control unit 410 causes the transmitting and receiving unit 409 to transmit the measurement result of the vein pattern to the authentication server 101 (S905), and the authentication server 101 authenticates the user. The control unit 410 receives the user authentication result from the authentication server 101 (S906). The control unit 410 determines whether or not the user authentication has been successful, based on the received authentication result (S907).

When it is determined that the user authentication has not been successful (NO in S907), the control unit 410 deletes information stored in a storage region of the storage unit 408 (S908), and proceeds to a process of starting over again the measurements of the blood sugar levels and the vein pattern (from S908 to S902). This leaves no measurement result of the third person other than the user in the blood sugar level measuring device 102. Thus, even when the user measures the blood sugar level of the user after the third person measures the blood sugar level of the third person, it is possible to prevent the measurement result of the user from mixing with the measurement result of the third person. As a result, the blood sugar level measuring device 102 makes it possible to prevent wrong transmission of the measurement results.

When it is determined that the user authentication has been successful (YES in S907), the control unit 410 causes the transmitting and receiving unit 409 to transmit, to the authentication server 101, the measurement result of the vein pattern and the measurement result of the blood sugar level in associate with each other (S909). Here, the control unit 410 sets, in data to be transmitted as shown in (b) in FIG. 6, the measurement result of the vein pattern and the measurement result of the blood sugar level, and transmits the data to the authentication server 101. It is to be noted that the measurement result of the blood sugar level to be transmitted to the authentication server 101 is an average of the four measurement results of the respective blood sugar levels. The measurement result of the vein pattern is used by the authentication server 101 to authenticate the user and can be shared as the ID for identifying the blood sugar level of each user. In other words, the control unit 204 of the authentication server 101 identifies the user by comparing the measurement result of the vein pattern transmitted from the blood sugar level measuring device 102 with the measurement result of the vein pattern stored in the blood sugar level management memory 203, and stores the measurement result of the blood sugar level in a storage region of "measurement log" assigned to the identified user. For this reason, it is not necessary to separately register, into the blood sugar level measuring device 102, an ID for identifying a blood sugar level. Thus, even when the user loses the blood sugar level measuring device 102, the third person cannot access the blood sugar level measuring device 102 to secretly look at personal information of the user. As a result, the blood sugar level measuring device 102 makes it possible to protect the privacy of the user.

After the process of transmitting the measurement results of the vein pattern and the blood sugar level (S909), the control unit 410 deletes information stored in the storage region of the storage unit 408 (S910). This does not leave the personal information of the user in the blood sugar level measuring device 102. Thus, even when the user loses the blood sugar level measuring device 102, the third person cannot access the blood sugar level measuring device 102 to secretly look at personal information of the user. As a result, the blood sugar level measuring device 102 makes it possible to protect the privacy of the user.

In this embodiment, in order to obtain the one measurement result of the blood sugar level, the blood sugar level measuring device 102 measures the blood sugar level the predetermined number of times in the predetermined measurement period, and determines the one measurement result of the blood sugar level by calculating the average of the measurement results obtained by performing the measurement the predetermined number of times. In addition, the blood sugar level measuring device 102 measures the vein pattern in the predetermined measurement period. With this, the blood sugar level measuring device 102 does not separate the blood sugar level measurements and the vein pattern measurement in terms of time but makes it possible to perform the measurements simultaneously. As a result, the blood sugar level measuring device 102 makes it possible to surely prevent the use of the measurement result of the blood sugar level of the third person as that of the user.

Figure 10:
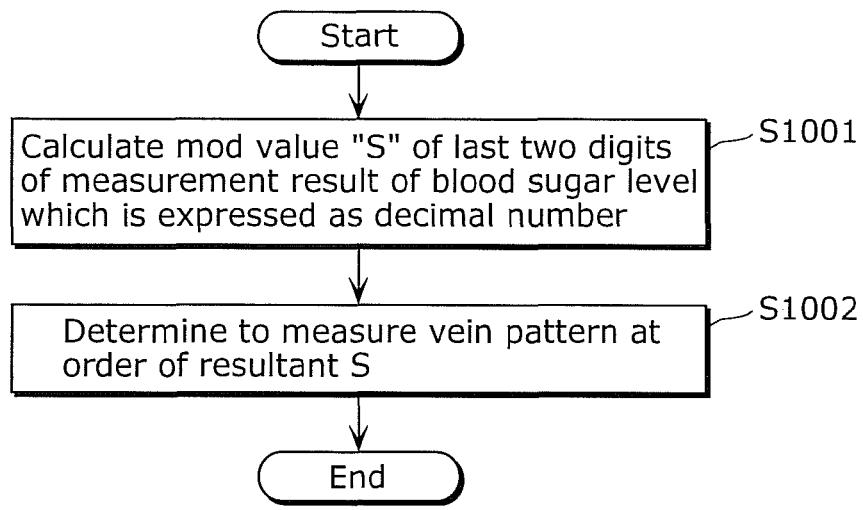
FIG. 10 is a flowchart showing in detail a measurement order determining process (S903 in FIG. 9).

FIG. 10 is a flowchart showing in detail the measurement order determining process (S903 in FIG. 9). In this process, for each predetermined measurement period for obtaining the one measurement result of the blood sugar level, the vein pattern measurement timing is changed based on the measurement result of the blood sugar level obtained in S902, and the order of measuring the blood sugar levels and the vein pattern are determined.

To put it differently, the control unit 410 expresses, as a decimal number, the first measurement result of the blood sugar level obtained in the blood sugar level measurement process (S902), and calculates a remainder "S" by dividing the last two digits of the decimal number by a total number of the remaining blood sugar measurements and the vein pattern measurement (hereinafter, simply referred to as "total number of measurements") "4". For instance, when the last two digits of the decimal number is 18, the remainder "S" is calculated as "S=18 mod 4=2". When the total number of measurements is "4", the remainder "S" may be an integer number ranging from 0 to 3.

Figure 11:
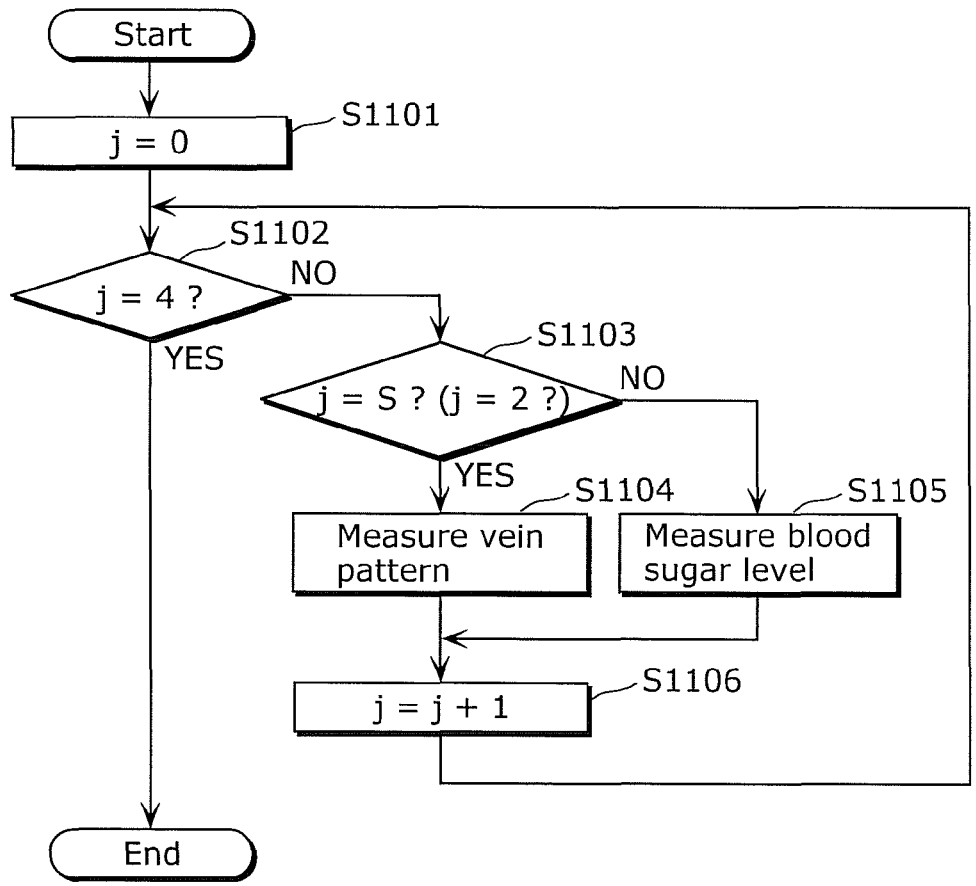
FIG. 11 is a flowchart showing in detail a measurement process (S904 in FIG. 9).

The control unit 410 determines to measure the vein pattern when a value of variable "j" is the remainder "S", in the processes of S1101 to S1106 shown in FIG. 11 (S1002). Stated differently, when the first measurement of the blood sugar level is not included in the number of measurements, the control unit 410 determines to measure the vein pattern the (S+1) time. For example, when the remainder "S" is "0", the control unit 410 determines to measure the vein pattern the first time, and when the remainder "S" is "2", the control unit 410 determines to measure the vein pattern the third time.

FIG. 11 is a flowchart showing in detail the measurement process (S904 in FIG. 9).

The control unit 410 sets "0" to the variable "j", and initializes the value of the variable "j" (S1101). The variable "j" is a variable for storing the number of measurements. More specifically, it means that when the first blood sugar level measurement is not included in the number of measurements and when the value of the variable "j" is "k", a measurement is to be performed the "k+1" time.

The control unit 410 proceeds to processes (S1102 to S1106) of measuring the blood sugar level three times and the vein pattern once based on the order determined in the process of S1002 shown in FIG. 10.

First, the control unit 410 determines whether or not the value of the variable "j" is equal to the total number of measurements "4" (S1102). When the value of the variable "j" is equal to the total number of measurements "4" (YES in S1102), the control unit 410 terminates this processing.

On the other hand, when the value of the variable "j" is not equal to the total number of measurements "4" (NO in S1102), the control unit 410 determines whether or not the value of the variable "j" is equal to the remainder "S" (S1103). More specifically, the value of the variable "j" is "0", and thus is not equal to the total number of measurements "4". Therefore, the flow moves to S1103.

When the value of the variable "j" is equal to the remainder "S" (YES in S1103), the calculating unit 407 measures the vein pattern (S1104). On the other hand, when the value of the variable "j" is not equal to the remainder "S" (NO in S1103), the calculating unit 407 measures the blood sugar level (S1105). More specifically, the value of the remainder "S" is "2", and thus is not equal to the value "0" of the variable "j". Therefore, the calculating unit 407 measures the blood sugar level (S1105).

After measuring the blood sugar level, the control unit 410 adds "1" to the variable "j" (S1106). This sets "1" to the variable "j". Then, the control unit 410 proceeds to a process for the second measurement (from S1106 to S1102).

The variable "j" is "1", and thus the value of the variable "j" is not equal to the value "2" of the remainder "S" (NO in S1103). Therefore, the calculating unit 407 measures the blood sugar level (S1105). After measuring the blood sugar level, the control unit 410 adds "1" to the variable "j" (S1106). This sets "2" to the variable "j". Then, the control unit 410 proceeds to a process for the third measurement (from S1106 to S1103).

The variable "j" is "2", and thus the value of the variable "j" is equal to the value "2" of the remainder "S" (YES in S1103). Thus, the calculating unit 407 measures the vein pattern (S1104). After measuring the vein pattern, the control unit 410 adds "1" to the variable "j" (S1106). This sets "3" to the variable "j" (S1106). Then, the control unit 410 proceeds to a process for the fourth measurement (from S1106 to S1104).

The variable "j" is "3", and thus the value of the variable "j" is not equal to the value "2" of the remainder "S" (NO in S1103). Thus, the calculating unit 407 measures the blood sugar level (S1105). After measuring the blood sugar level, the control unit 410 adds "1" to the variable "j" (S1106). This sets "4" to the variable "j" (S1106). Here, the value of the variable "j" has reached the total number of measurements "4" (YES in S1102), and thus the control unit 410 terminates the processing.

As stated above, when the processes of S1102 to S1106 are repeated until the value of the variable "j" reaches the total number of measurements "4" in S1102, the blood sugar level is measured the first, second, and fourth times of the processing, and the vein pattern is measured the third time. A vein pattern measurement timing randomly changes in the measurement period "T". For instance, as shown in (a) in FIG. 13, the vein pattern is measured the fourth time in the first measurement period "T". Moreover, as shown in (b) in FIG. 13, the vein pattern is measured the second time in the second measurement period "T". Furthermore, as shown in (c) in FIG. 13, the vein pattern is measured the third time in the third measurement period "T".

According to this embodiment, the blood sugar level measuring device 102 makes it possible to randomly change, for each predetermined measurement period for obtaining the one measurement result of the blood sugar level, the vein pattern measurement timing. With this, the user cannot distinguish between the vein pattern measurement timing and the blood sugar level measurement timing. Therefore, the third person cannot replace the finger of the user by the finger of the third person and measure the blood sugar level during the blood sugar level measurement. As a result, the blood sugar level measuring device 102 makes it possible to surely prevent the use of the measurement result of the blood sugar level of the third person as that of the user.

Furthermore, the authentication server 101 performs authentication using the measurement result of the vein pattern, and thus the authentication server 101 makes it possible to identify the user by using the measurement result of the vein pattern obtained for each blood sugar level measuring device 102, instead of the user ID pre-set to the blood sugar level measuring device 102. This does not leave the personal information of the user in the blood sugar level measuring device 102. Thus, even when the user loses the blood sugar level measuring device 102, the third person cannot access the blood sugar level measuring device 102 to secretly look at the personal information of the user. As a result, the blood sugar level measuring device 102 according to this embodiment makes it possible to protect the privacy of the user.

Moreover, according to this embodiment, in order to obtain the one measurement result of the blood sugar level, the blood sugar level measuring device 102 measures the blood sugar level the predetermined number of times in the predetermined measurement period, and calculates the average of the measurement results obtained by performing the measurement the predetermined number of times. In addition, the blood sugar level measuring device 102 measures the vein pattern in the predetermined measurement period. With this, the blood sugar level measuring device 102 does not separate the blood sugar level measurement and the vein pattern measurement in terms of time but makes it possible to perform the measurements continuously. For this reason, it is possible to prevent replacement of the measurement result of the blood sugar level of the user with that of the third person. For example, when a patient has a bad health condition at the time of applying for an insurance policy, there is a possibility that an insurance company rejects the application due to the bad health condition of the patient. To avoid this, it is considered that the patient transmits, using an ID of the patient, a test result of another person having a good health condition, to a server of the insurance company, and applies for the insurance policy using the test result. However, according to this embodiment, it is possible to surely prevent such a fraud.

Moreover, according to this embodiment, the blood sugar level measuring device 102 measures, in the predetermined measurement period, the blood sugar level the first time and the vein pattern the second time or subsequent to the second time. With this, the vein pattern is not measured the first time. Thus, after measuring the vein pattern of the user the first time, it is not possible to replace the finger of the user by the finger of the third person and measure the blood sugar level of the third person the second time onward. As a result, it is possible to surely prevent the use of the measurement result of the blood sugar level of the third person as that of the user.

Moreover, according to this embodiment, the blood sugar level measuring device 102 transmits the measurement result of the vein pattern to the authentication server 101. When the authentication server 101 successfully authenticates the user by using the measurement result of the vein pattern, the blood sugar level measuring device 102 transmits, to the authentication server 101, the measurement result of the vein pattern and the measurement result of the blood sugar level in association with each other. With this, the measurement result of the vein pattern is used by the authentication server 101 to authenticate the user and can be also used as the ID for identifying the blood sugar level of each user. For this reason, it is not necessary to separately register, into the blood sugar level measuring device 102, the ID for identifying the blood sugar level. Thus, even when the user loses the blood sugar level measuring device 102, the third person cannot access the blood sugar level measuring device 102 to secretly look at personal information of the user. As a result, the blood sugar level measuring device 102 makes it possible to protect the privacy of the user.

Moreover, according to this embodiment, after transmitting the measurement result of the blood sugar level and the measurement result of the vein pattern to the authentication server 101, the blood sugar level measuring device 102 deletes the measurement result of the blood sugar level and the measurement result of the vein pattern therefrom. This does not leave the personal information of the user in the blood sugar level measuring device 102. Thus, even when the user loses the blood sugar level measuring device 102, the third person cannot access the blood sugar level measuring device 102 to secretly look at the personal information of the user. As a result, the blood sugar level measuring device 102 makes it possible to protect the privacy of the user.

Moreover, according to this embodiment, when the authentication server 101 fails to authenticate the user, the blood sugar level measuring device 102 deletes the measurement result of the blood sugar level and the measurement result of the vein pattern therefrom, without transmitting, to the authentication server 101, the measurement result of the blood sugar level and the measurement result of the vein pattern. This leaves no measurement result of the third person other than the user in the blood sugar level measuring device 102. Thus, even when the user measures the blood sugar level of the user after the third person measures the blood sugar level of the third person, it is possible to prevent the measurement result of the user from mixing with the measurement result of the third person. As a result, the blood sugar level measuring device 102 makes it possible to prevent the wrong transmission of the measurement results.

Moreover, according to this embodiment, at the time of the initial user ID registration, the blood sugar level measuring device 102 transmits the user ID and the measurement result of the vein pattern to the authentication server 101. This allows the authentication server 101 to associate the user ID with the measurement result of the vein pattern. For this reason, the measurement result of the vein pattern measured each time the blood sugar level is measured is used by the authentication server 101 to authenticate the user and can be also used as the ID for identifying the blood sugar level of each user. Thus, since it is not necessary to have separately registered, into the blood sugar level measuring device 102, the ID for identifying the blood sugar level, even when the user loses the blood sugar level measuring device 102, the third person cannot access the blood sugar level measuring device 102 to secretly look at the personal information of the user. As a result, the blood sugar level measuring device 102 makes it possible to protect the privacy of the user.

Although the biological information measuring system according to this embodiment of the present invention has been described, the present invention is not limited to this embodiment.

For instance, this embodiment has described the example using the blood sugar level as one example of the biological data, the present invention is not limited to this. As long as biological data can be measured through light emission by a light source, the present invention can be appropriately applied. For example, the present invention can be applied to measurement of oxygen saturation in blood.

In this embodiment, as the method for determining the vein pattern measurement timing, the measurement result of the blood sugar level obtained in S902 is expressed as the decimal number and the remainder obtained by dividing the decimal number by the predetermined value is used (S1001), any method in which the vein pattern measurement timing randomly changes for each predetermined measurement period may be used. For instance, the vein pattern measurement timing may be determined using not the measurement result of the blood sugar level but a time, air temperature, body temperature, and so on.

Moreover, although the average of the measurement results of the respective blood sugar levels obtained by performing the measurement the predetermined number of times is used as the measurement result of the blood sugar level in this embodiment, an other value may be used. For example, the median among the blood sugar levels obtained by performing the measurement the predetermined number of times may be used as the measurement result of the blood sugar level. In addition, the last measurement result of the blood sugar level among the blood sugar levels obtained by performing the measurement the predetermined number of times may be used as the measurement result of the blood sugar level. This allows the stable blood sugar level to be used as the measurement result.

Moreover, although the user ID is initially registered into the blood sugar level measuring device 102 on a temporary basis and the user ID and the measurement result of the vein pattern are transmitted to the authentication server 101 in this embodiment, the user ID may not be initially registered into the blood sugar level measuring device 102. In this case, the blood sugar level measuring device 102 may transmit only the measurement result of the vein pattern to the authentication server 101, and the authentication server 101 may issue an user ID and may associate the issued user ID and the received measurement result of the vein pattern with each other, thereby performing the initial user ID registration.

Figure 12:
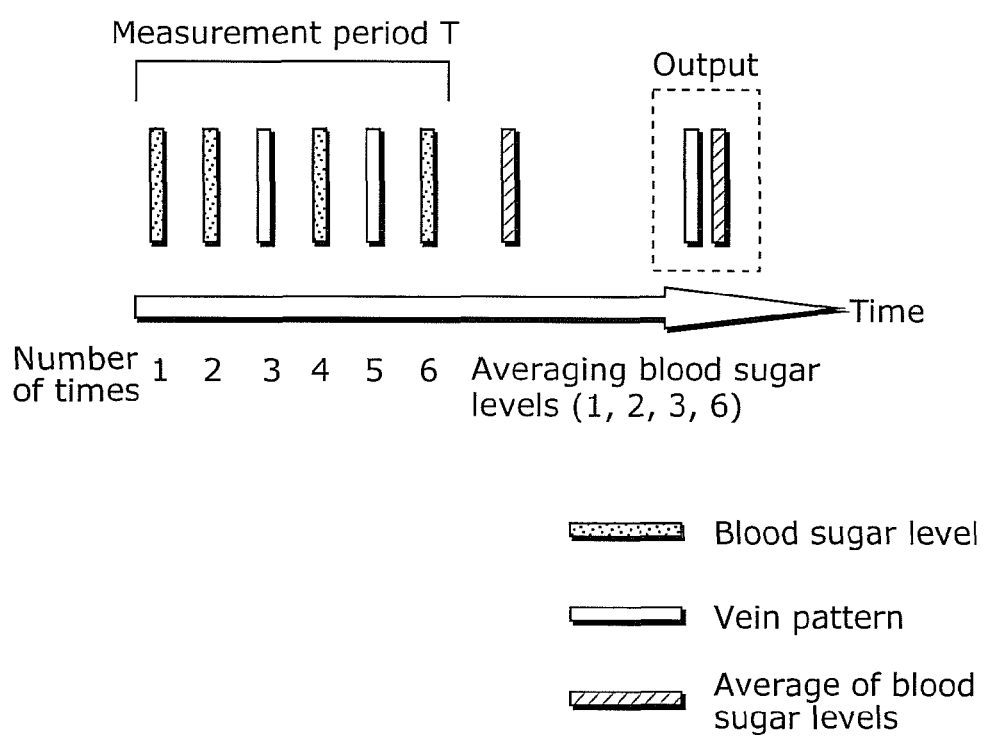
FIG. 12 is a diagram for illustrating a blood sugar level measurement principle used by the blood sugar level measuring device according to the embodiment of the present invention.

Moreover, although, as shown in FIG. 8, the vein pattern is measured once in the predetermined measurement period "T" in this embodiment, the vein pattern may be measured plural times. For example, when the vein pattern is measured two times in the predetermined measurement period "T", a vein pattern measurement timing may be randomly determined through a method described below. For instance, when the blood sugar level and the vein pattern are measured remaining three times and two times, respectively, the control unit 410 performs the following process instead of the process of S1002 shown in FIG. 10. In other words, as shown in FIG. 12, the control unit 410 calculates the remainder "S" by dividing a value of the first measurement result of the blood sugar level, which is expressed as a decimal number, by the total number of measurements "5". When the first blood sugar level measurement is not included in the number of measurements, it is determined that the first vein pattern measurement is to be performed with a timing following the S-th blood sugar level measurement. FIG. 12 indicates a case where "S" is "1", and the first vein pattern measurement is performed with a timing following the first blood sugar level measurement. Next, the control unit 410 determines the second vein pattern measurement timing. Stated differently, the control unit 410 determines with which timing the vein pattern is to be measured between the remaining blood sugar level measurements. In the example shown in FIG. 12, at a moment when the first vein pattern measurement is completed, the total number of measurements is "3". Accordingly, for example, the remainder "S2" is calculated by dividing the value of the first vein pattern measurement, which is expressed as the decimal number, by the total number of measurements "3". With this, the control unit 410 determines that the second vein pattern measurement is to be performed with a timing following the S2-th blood sugar level measurement. FIG. 12 indicates a case where "S2" is "1". The blood sugar level measuring device 102 measures the vein pattern with the determined timing.

It is to be noted that, when the vein pattern is measured the plural times, plural measurement results of respective vein patterns may be transmitted to the authentication server 101. In this case, only when all the measurement results of the respective vein patterns match the vein pattern registered in advance, the authentication server 101 may determine that the authentication has been successful. In addition, only when all the measurement results of the respective vein patterns match each other after the blood sugar level measuring device 102 compares the measurement results of the respective vein patterns with each other, the blood sugar level measuring device 102 may transmit, to the authentication server 101, any measurement results of the respective vein patterns.

Moreover, although the light-receiving unit 404 receives the transmitted light which is the first infrared light transmitted through the finger in this embodiment, the light-receiving unit 404 may receive reflected light which is the first infrared light reflected from the user's finger inserted into the finger insertion part 401. In this case, the calculating unit 407 measures a vein pattern based on the reflected light of the first infrared light.

Moreover, although the light-receiving unit 405 receives the reflected light which is the second infrared light reflected from the finger in this embodiment, the light-receiving unit 405 may receive transmitted light which is the second infrared light transmitted through the user's finger inserted into the finger insertion part 401. In this case, the calculating unit 407 measures a blood sugar level of the user based on the transmitted light of the second infrared light.

Each of the above devices may be specifically a computer system including a micro processing unit, a ROM, a RAM, a hard disk drive, a display unit, a keyboard, a mouse, and so on. A computer program is stored in the RAM or the hard disk drive. The micro processing unit operates according to the computer program, so that each device fulfils its functions. Here, in order to fulfill predetermined functions, the computer program is programmed by combining plural instruction codes each of which indicates an instruction for a computer. For instance, the storage unit 408 of the blood sugar level measuring device 102 may include the RAM, and the switching unit 406, the calculating unit 407, the transmitting and receiving unit 409, and the control unit 410 may be implemented by executing the computer program.

Furthermore, part or all of the elements included in each device may be included in one system LSI (Large Scale Integration). The system LSI is a super-multifunctional LSI manufactured by integrating components on one chip and is, specifically, a computer system including a micro processing unit, a ROM, a RAM, and the like. A computer program is stored in the RAM. The micro processing unit operates according to the computer program, so that the system LSI fulfils its functions. For example, the switching unit 406, the calculating unit 407, the transmitting and receiving unit 409, and the control unit 410 may be included in an integrated circuit.

Moreover, part or all of the elements included in each device may be included in an IC card removable from each device or in a stand alone module. The IC card or the module is a computer system including a micro processing unit, a ROM, a RAM, and the like. The IC card or the module may include the above super-multifunctional LSI. The micro processing unit operates according to a computer program, so that the IC card or the module fulfils its functions. The IC card or the module may have tamper-resistance.

Furthermore, the present invention may be any of the above methods. Moreover, the present invention may be a computer program which causes a computer to execute these methods, and a digital signal which is composed of the computer program.

Furthermore, in the present invention, the computer program or the digital signal may be recorded on a computer-readable recording medium such as a flexible disk, a hard disk, a CD-ROM, an MO, a DVD, a DVD-ROM, a DVD-RAM, a BD (Blu-ray Disc™), and a semiconductor memory. In addition, the digital signal may be recorded on these recording media.

Moreover, in the present invention, the computer program or the digital signal may be transmitted via an electronic communication line, a wireless or wired communication line, a network represented by the Internet, data broadcasting, and the like.

Furthermore, the present invention may be a computer system including a micro processing unit and a memory. The memory may store the above computer program, and the micro processing unit may operate according to the computer program.

Moreover, the present invention may execute the computer program or the digital signal in another independent computer system by recording the computer program or the digital signal on the recording medium and transmitting the recorded computer program or the digital signal or by transmitting the computer program or the digital signal via the network and the like.

Furthermore, the above embodiment and the above modifications may be combined, respectively.

It should be considered that the embodiment disclosed herein are exemplary in all respects and not restrictive at all. It is intended that the scope of the present invention is indicated by not the above description of the embodiment but the claims, and that any change that has equivalent meaning as and fall within the claims are included.

The present invention can be applied to the blood sugar level measuring device which is capable of protecting the privacy of the user and preventing the replacement of the user's test result with the somebody else's test result, and the control method thereof.

REFERENCE SIGNS LIST

101 Authentication server
102 Blood sugar level measuring device
201 Transmitting and receiving unit
202 Authenticating unit
203 Blood sugar level management memory
204 Control unit
401 Finger insertion part
402 Light source
403 Light source
404 Light-receiving unit
405 Light-receiving unit
406 Switching unit
407 Calculating unit
408 Storage unit
409 Transmitting and receiving unit
410 Control unit

The invention claimed is:

1. A biological information measuring device comprising:
    a finger insertion part into which a finger of a user is inserted;
    a first light source which emits, to the finger insertion part, a first light having a first wavelength;
    a second light source which emits, to the finger insertion part, a second light having a second wavelength different from the first wavelength;
    a first light-receiving unit configured to receive a first reception light which is the first light transmitted through the finger or reflected from the finger;
    a second light-receiving unit configured to receive a second reception light which is the second light transmitted through the finger or reflected from the finger;
    a calculating unit configured to measure a vein pattern of the user based on the first reception light, and measure biological data of the user based on the second reception light, the biological data being different from the vein pattern;
    a transmitting and receiving unit configured to transmit, to an external server, a measurement result of the biological data in association with a measurement result of the vein pattern; and
    a control unit configured to determine a timing at which the vein pattern of the user is to be measured so that the timing changes for each predetermined measurement period,
    wherein the calculating unit is configured to measure the biological data a predetermined number of times in a predetermined measurement period, determine a value obtained from the measurement results of the biological data measured the predetermined number of times as one measurement result of biological data, and measure the vein pattern in the predetermined measurement period, and
    the measurement result of the vein pattern is used by the server to authenticate the user, and is shared as a identifier for identifying the biological data of the user.

2. The biological information measuring device according to claim 1,
    wherein the control unit is configured to determine the timing so that the timing randomly changes for each predetermined measurement period.

3. The biological information measuring device according to claim 2,
    wherein the calculating unit is configured to measure the biological data of the user's first time in the predetermined measurement period, and
    the control unit is configured to determine the timing based on a first measurement result of the biological data of the user measured by the calculating unit.

4. The biological information measuring device according to claim 1,
    wherein the calculating unit is configured to determine the one measurement result of the biological data by calculating an average of the measurement results of the biological data measured the predetermined number of times.

5. The biological information measuring device according to claim 1,
    wherein the calculating unit is configured to determine the one measurement result of the biological data by selecting any one of the measurement results of the biological data measured the predetermined number of times.

6. The biological information measuring device according to claim 5,
    wherein the calculating unit is configured to determine a median of the measurement results of the biological data measured the predetermined number of times as the one measurement result of the biological data.

7. The biological information measuring device according to claim 1,
    wherein the control unit is configured to delete, from the biological information measuring device, the measurement result of the vein pattern and the measurement result of the biological data after the measurement result of the vein pattern and the measurement result of the biological data are transmitted to the server.

8. The biological information measuring device according to claim 1,
    wherein the transmitting and receiving unit is further configured to receive, from the server, an authentication result of the user obtained by using the transmitted measurement result of the vein pattern, and
    when the authentication result received from the server by the transmitting and receiving unit indicates that the user has been successfully authenticated, the control unit is further configured to transmit, to the server, the measurement result of the vein pattern and the measurement result of the biological data in association with each other.

9. The biological information measuring device according to claim 8, wherein, when the authentication result received from the server by the transmitting and receiving unit indicates that the user has not been successfully authenticated, the control unit is further configured to delete, from the biological information measuring device, the measurement result of the vein pattern and the measurement result of the biological data, without transmitting the measurement result of the vein pattern and the measurement result of the biological data to the server.

10. The biological information measuring device according to claim 1, wherein, prior to transmitting the first measurement result of the vein pattern and the measurement result of the biological data, the control unit is configured to transmit, to the server, the measurement result of the vein pattern of the user and an identifier of the user set to the biological information measuring device.

11. The biological information measuring device according to claim 1, wherein the first light is infrared light having the first wavelength of 760 nm, and the second light is infrared light having the second wavelength of 1300 nm.

12. The biological information measuring device according to claim 1, wherein the biological data is a blood sugar level.

13. A control method of a biological information measuring device which measures biological information of a user, wherein the biological information measuring device includes:
a finger insertion part into which a finger of the user is inserted;
a first light source which emits, to the finger insertion part, a first light having a first wavelength;
a second light source which emits, to the finger insertion part, a second light having a second wavelength different from the first wavelength;
a first light-receiving unit configured to receive a first reception light which is the first light transmitted through the finger or reflected from the finger;
a second light-receiving unit configured to receive a second reception light which is the second light transmitted through the finger or reflected from the finger,
the control method comprising:
determining a timing at which a vein pattern of the user is to be measured so that the timing changes for each predetermined measurement period;
measuring a vein pattern of the user based on the first reception light received by the first light-receiving unit;
measuring biological data of the user based on the second reception light received by the second light-receiving unit, the biological data being different from the vein pattern; and
transmitting, to an external server, a measurement result of the biological data in association with a measurement result of the vein pattern,
in the measuring of biological data, the biological data is measured a predetermined number of times in a predetermined measurement period, and a value obtained from the measurement results of the biological data measured the predetermined number of times is determined as one measurement result of biological data, and
in the measuring of a vein pattern, the vein pattern of the user is measured with the determined timing in the predetermined measurement period, and
the measurement result of the vein pattern is used by the server to authenticate the user, and is shared as a identifier for identifying the biological data of the user.

14. A non-transitory computer-readable recording medium for use in a computer, the recording medium having a computer program recorded thereon for causing the computer to execute:
determining a timing at which a vein pattern of a user is to be measured so that the timing changes for each predetermined measurement period;
measuring a vein pattern of a user based on transmitted light or reflected light, the transmitted light being a first light having a first wavelength that is emitted to a finger insertion part by a first light source and transmitted through a finger of the user, the reflected light being the first light reflected from the finger, and the finger being inserted into the finger insertion part;
measuring biological data of the user based on transmitted light or reflected light, the transmitted light being a second light having a second wavelength that is emitted to the finger insertion part by a second light source and transmitted through the finger, the reflected light being the second light reflected from the finger, and the second wavelength being different from the first wavelength, the biological data being different from the vein pattern; and
transmitting, to an external server, a measurement result of the biological data in association with a measurement result of the vein pattern,
wherein in the measuring of biological data, the biological data is measured a predetermined number of times in a predetermined measurement period, and a value obtained from the measurement results of the biological data measured the predetermined number of times is determined as one measurement result of biological data,
in the measuring of a vein pattern, the vein pattern of the user is measured with the determined timing in the predetermined measurement period, and
the measurement result of the vein pattern is used by the server to authenticate the user, and is shared as a identifier for identifying the biological data of the user.

15. An integrated circuit comprising:
a calculating unit configured to (i) measure a vein pattern of a user based on transmitted light or reflected light, the transmitted light being a first light having a first wavelength that is emitted to a finger insertion part by a first light source and transmitted through a finger of the user, the reflected light being the first light reflected from the finger, and the finger being inserted into the finger insertion part, and (ii) measure biological data of the user based on transmitted light or reflected light, the transmitted light being a second light having a second wavelength that is emitted to the finger insertion part by a second light source and transmitted through the finger, the reflected light being the second light reflected from the finger, the second wavelength being different from the first wavelength, and the biological data being different from the vein pattern;

a transmitting and receiving unit configured to transmit, to an external server, a measurement result of the biological data in association with a measurement result of the vein pattern;

a control unit configured to determine a timing at which the vein pattern of the user is to be measured so that the timing changes for each predetermined measurement period, wherein the calculating unit is configured to measure the biological data a predetermined number of times in a predetermined measurement period, determine a value obtained from the measurement results of the biological data measured the predetermined number of times as one measurement result of biological data, and measure the vein pattern in the predetermined measurement period, and the measurement result of the vein pattern is used by the server to authenticate the user, and is shared as a identifier for identifying the biological data of the user.

16. A biological information measuring system comprising a biological information measuring device which measures biological information of a user and a server which receives the biological information measured by the biological information measuring device and registers the received biological information into a database, wherein the biological information measuring device includes:

a finger insertion part into which a finger of the user is inserted;

a first light source which emits, to the finger insertion part, a first light having a first wavelength;

a second light source which emits, to the finger insertion part, a second light having a second wavelength different from the first wavelength;

a first light-receiving unit configured to receive a first reception light which is the first light transmitted through the finger or reflected from the finger;

a second light-receiving unit configured to receive a second reception light which is the second light transmitted through the finger or reflected from the finger;

a calculating unit configured to measure a vein pattern of the user based on the first reception light, and measure biological data of the user based on the second reception light, the biological data being different from the vein pattern;

a transmitting and receiving unit configured to transmit, to the server, a measurement result of the biological data in association with a measurement result of the vein pattern; and a control unit configured to determine a timing at which the vein pattern of the user is to be measured so that the timing changes for each predetermined measurement period, wherein the calculating unit is configured to measure the biological data a predetermined number of times in a predetermined measurement period, determine a value obtained from the measurement results of the biological data measured the predetermined number of times as one measurement result of biological data, and measure the vein pattern in the predetermined measurement period, and the measurement result of the vein pattern is used by the server to authenticate the user, and is shared as a identifier for identifying the biological data of the user, and the server includes:

a transmitting and receiving unit configured to receive, from the biological information measuring device, the measurement result of the vein pattern and the measurement result of the biological data;

a memory which stores, for each user, a measurement result of a vein pattern in advance; and a control unit configured to write, when the measurement result of the vein pattern received by the transmitting and receiving unit matches the measurement result of the vein pattern stored in advance in the memory, the measurement result of the vein pattern received by the transmitting and receiving unit in association with the measurement result of the vein pattern stored in advance in the memory, into the memory.

\* \* \* \* \*